United States Patent [19]
Park et al.

[11] Patent Number: 6,013,832
[45] Date of Patent: Jan. 11, 2000

[54] PROCESS FOR THE PRODUCTION OF BENZENE DERIVATIVES

[75] Inventors: Sang Hoo Park, Yongin; Maeng Sup Kim, Seoul; Sung Min Cho; Ki Sug Kim, both of Yongin; Jeong Soo Kim, Seoul; Eun Jung Cho, Gunpo; Tae Gun Choi, Kyunggi-do; In Soo Park, Yongin, all of Rep. of Korea

[73] Assignee: Kolon Industries, Inc., Kwacheon, Rep. of Korea

[21] Appl. No.: 08/993,018

[22] Filed: Dec. 18, 1997

[30]     Foreign Application Priority Data

Jul. 4, 1997 [KR]   Rep. of Korea ...................... 97-31040

[51] Int. Cl.$^7$ .................................................. C07C 69/76
[52] U.S. Cl. ........................................... 560/105; 562/496
[58] Field of Search .............................. 562/496; 560/105

[56]                References Cited

U.S. PATENT DOCUMENTS

| | | |
|---|---|---|
| 3,919,206 | 11/1975 | Patchornik et al. . |
| 5,026,687 | 6/1991 | Yarchoan et al. .......................... 514/45 |
| 5,073,627 | 12/1991 | Curtis et al. .............................. 530/351 |
| 5,116,964 | 5/1992 | Capon et al. ............................... 536/27 |
| 5,225,538 | 7/1993 | Capon et al. ............................. 530/387 |
| 5,349,053 | 9/1994 | Landolfi .................................... 530/351 |
| 5,409,698 | 4/1995 | Anderson et al. ....................... 424/85.2 |
| 5,419,900 | 5/1995 | Lane et al. .............................. 424/85.2 |
| 5,428,130 | 6/1995 | Capon et al. ............................. 530/350 |
| 5,503,841 | 4/1996 | Doyle et al. .......................... 424/278.1 |
| 5,521,288 | 5/1996 | Linsley et al. ........................ 530/387.3 |
| 5,580,859 | 12/1996 | Felgner et al. ............................. 514/44 |
| 5,593,972 | 1/1997 | Weiner et al. .............................. 514/44 |
| 5,643,578 | 7/1997 | Robinson et al. .................... 424/210.1 |
| 5,656,297 | 8/1997 | Bernstein et al. ....................... 424/484 |
| 5,693,762 | 12/1997 | Queen et al. ......................... 530/387.3 |

FOREIGN PATENT DOCUMENTS

| | | |
|---|---|---|
| WO 95/21258 | 8/1995 | European Pat. Off. . |
| WO 97/30039 | 10/1996 | European Pat. Off. . |
| WO 97/14433 | 4/1997 | European Pat. Off. . |

OTHER PUBLICATIONS

Phase Transfer Catalyst principles and technique; Starks et al, pp. 1–11, 1981.

Kuby, Janis, *Chapter 11 Immunology*, W. H. Freeman and Co., (1992).

Engelhard, Victor H., "How Cells Process Antigens.", *Scientific American*, Aug. 1994.

Chow, Yen–Hung, et al. "Improvement of Hepatitis B Virus DNA Vaccines by Plasmids Coexpressing Hepatitis B surface Antigen and Interleukin–2" *J. Virol.*, 71 (1):169–178, 1997.

Xiang, et al. "Manipulation of the Immune Response to a Plasmid–Encoded Viral Antigen by Coinoculation with Plasmids Expressing Cytokines," *Immunity*, 2:129–135, (1995).

Conry, R. M. et al. "Selected Strategies to Augment Polynucleotide Immunization." *Gene Therapy*, 3:67–74 (1996).

Iwasaki, A. et al. "Enhanced CTL Responses Medicated by Plasmid DNA Immunogens Encoding Costimulatory Molecules and Cytokines." *J. Immunol.*,158:4591–4601 (1997).

Geissler, M., et al. "Enhancement of Cellular and Humoral Immune Responses by Hepatitis C. Virus Core Protein Using DNA–Based Vaccines Augmented with Cytokine–Expressing Plasmids." *J. Immonol.*, 158:1231–1237 (1997).

Kim, J. J., et al. "In Vivo Engineering of Cellular Immune Response by Coadministration ofIL–12 Expression Vector with a DNA Immunogen." *J. Immunol*, 158:816 826 (1997).

Rosenberg, S. A., et al. "Immunologic and Therapeutic Evaluation of a Synthetic Peptide Vaccine for the Treatment of Patients with Metastatic Melanoma." *Nature Medicine*, 4(3):321–327 (1998).

Wolff, J. A., et al. "Direct Gene Transfer Into Mouse Muscle in Vivo." *Science* (*Wash DC*). 247:1465–1468.

Tang, D. C., et al. "Genetic Immunization Is A Simple Method for Eliciting an Immuno Response." *Nature* (*Lond.*) 356:152–154.

Ulmer, J. B., et al. "Heterologous Protection Against Influenza by Injection of DNA Encoding a Viral Protein." *Science* (*Wash. DC*). 259:1745–1749 (1993).

Wang, B., et al. "Gene Inoculation Generates Immune Responses Against Human Immunodeficiency Virus Type 1." *Proc. Natl. Acad. Sci. USA*. 90:4156–4160 (1993).

Fynan, E. F., et al. "DNA Vaccines: Protective Immunizatins by Parenteral, Mucosal, and Gene–Gun Inoculations." *Proc. Natl. Acad. Sci. USA*. 90:11478–11482 (1993).

Ulmer, J. B., et al., "Protective Immunity by Intramuscular Injection of Low Doses of Influenza Virus DNA Vaccines." *Vaccine* 12:1541–1544 (1994).

Donnelly, J. J., et al. "Preclinical Efficacy of a Prototype DNA Vaccine: Enhance Protection Against Antigenic Drift in Influenza Virus." *Nature Med.*, 1:583–587 (1995).

(List continued on next page.)

*Primary Examiner*—Samuel Barts
*Attorney, Agent, or Firm*—Oblon, Spivak, McClelland, Maier & Neustadt, P.C.

[57]                ABSTRACT

The present invention relates to a process for the production of benzene derivatives represented by formula (I), which are useful as intermediates for agricultural chemicals, fine chemical products or pharmaceuticals such as anti inflammatory analgesics. The process includes reacting a compound of chemical formula (II) with a hydroformylating agent and a halogenating agent.

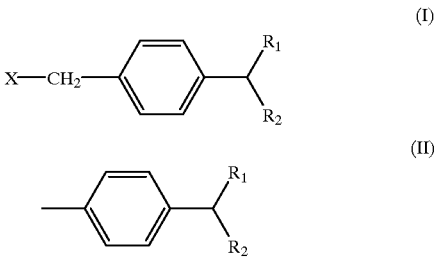

19 Claims, No Drawings

OTHER PUBLICATIONS

Cohen, J., "Naked DNA Points the Way to Vaccines." *Science (Wash. DC)* 259:1691–1692 (1993).

Donnelly, J. J., et al., "Immuization with DNA." *J. Immunol, Methods.* 176:145–152 (1994).

Ertl, H. C., et al. "Novel Vaccine Approaches." *J. Immunol.* 156:3579–3582 (1996).

McDonnell, W. M., et al. "DNA Vaccines." *N. Engl. J. Med.* 334:42–45 (1996).

Baltimore, D., "Lessons from People with Nonprogressive HIV Infection." *N. Engl. J. Med.*, 332:259–260 (1995).

Cao, Y., et al., "Virologic and Immunologic Characterization of Long–Term Survivors of Human Immunodeficiency Virus Type 1 Infection." *N. Engl. J. Med.* 332:201–208 (1995).

Haynes, B. F., et al. "Toward an Understanding of the Correlates of Protective Immunity to HIV Infection." *Science (Wash. DC)*. 271:324–328 (1996).

Musey, L., et al. "Cytotoxic T–Cell Responses, Viral Load and Disease Progression in Early Human Immunodeficiency Virus Type 1 Infection." *N. Engl. J. Med.*, 337:1267–1274 (1997).

Wang, B., et al. "DNA Inoculation Induces Neutralizing Immune Responses Against Human Immunodeficiency Virus type 1 in Mice and Nonhuman Primates." *DNA Cell Biol.* 12:799–80 (1993).

Shiver, J., W., et al. "Cytotoxic T Lymphocyte and Helper T Cell Responses Following HIV Polynucleotide Vaccination." *Ann. NY Acad. Sci.* 772:198–208 (1995).

Wang, B., et al. "Induction of Humoral and Cellular Immune Responses to the Human Immunodeficiency Type 1 Virus in Nonhuman Primates by in Vivo DNA Inoculation." *Virology*, 211:102–112 (1995).

Shiver, J. W., et al. "Humoral and Cellular Immunities Elicited by HIV–1 DNA Vaccination." *J. Pharm. Sci.* 85:1317–1324 (1996).

Liu, M. A., et al. "Vaccination of Mice and Nonhuman Primates Using HIV Gene Contain DNA." *Antibiot. Chemother.* 48:100–104 (1996).

Yasutomi, Y., et al. "Simian Immunodeficiency Virus–Specific Cytotoxic T–Lymphocyte Induction through DNA Vaccination of Rheses Monkeys." *J. Virol.* 70:678–681 (1996).

Lekutis, C., et al. "HIV–1 Env DNA Vaccine Administered to Rhesus Monkeys Elicits MHC Class II–Restricted CD4 T Helper Cells that Secrete IFN–$\gamma$ and TNF–$\alpha$." *J. Immunol.* 158:4471–4477 (1997).

Lu, S., "Simian Immunodeficiency Virus DNa Vaccine Trial in Macaques." *J. Virol.* 70:3978–3991 (1996).

Boyer, J. D., et al. "Protection of Chimpanzees from High–Dose Heterolgous HIV–1 Challenge by DNA Vaccination." *Nature Med.*, 3:526–532 (1997).

Kennedy, R. C., "DNA Vaccination for HIV." *Nature Med.* 3:501–502 (1997).

Letvin, N. L., et al. "Potent, Protective Anti–HIV Immune Responses Generated by Bimodal HIV Envelope DNA Plus Protein Vaccination." *Proc. Natl. Aca. Sci. USA.* 94:9379–9383 (1997).

Tsuji, T., et al. "Enhancement of Cell–Mediated Immunity Against HIV–1 Induced by Coinoculation of Plasmid–Encoded HIV–1 Antigen with Plasmid Expressing IL–12." *J. Immunol.* 158:4008–4013 (1997).

Okada, E., et al. Intranasal Immunization of a DNA Vaccine with IL–12– and Granulocyte–Macrophage Colony–Stimulated Factor (GM–SCF)–Expressing Plasmids in Liposomes Induces Strong Mucosal and Cell–Mediated Immune Responses Against HIV–1 Antigens.: *J. Immunol.* 159:5107–5113 (1997).

Geissler, M., et al. "Inhibitory Effects of Chronic Ethanol Consumption on Cellular Immune Responses to Hepatitis C Virus Core Protein are Reversed by Genetic Immunizations Augmented with cytokine–Expressing Plasmids." *J. Immunol.* 159:5107–5113 (1997).

Raz, E., et al. "Systemic Immunological Effects of Cytokine Genes Injected into Skeletal Muscle." *Proc. Natl. Aca. Sci. USA.* 90:4523–4257 (1993).

Landolfi, N. F., "A chimeric IL–2/Ig Molecule Possess the Functional Activity of Both Proteins." *J. Immunol.* 146:915–919 (1991).

Zheng, X. X., et al. "Administration of Noncytolytic IL–10/Fc in Murine Models of Lipopolysaccharide–Induced Septpic Shock and Allogeneic Islet Transplantation." *J. Immunol.* 154: 5590–5600 (1995).

Nickerson, P., et al. "Prolonged Islet Allograft Acceptance in the Absence of Interleukin 4 Expression." *Transpl Immunol.* 4:81–85 (1996).

Montgomery, D. L., et al. "Heterologous and Homologous Protection Against Influenza A by DNA Vaccination: Optimization of DNA Vectors." *DNA and Cell Bio.* 12:777–783 (1993).

Chapman, B. S., et al. "Effect of Intron A from Human Cytomegalovirus (Towne) Immediate–Early Gene on Heterologous Expression in Mammalian Cells." *Nuc. Acids Res* 19:3979–3986 (1991).

Davies, M. V., et al. "The Sequence Context of the Initiation Codon in the Encephalomyocarditis Virus Leader Modulates Efficiency of Internal Translation Initiation." *J. Virol.* 66:1924–1932 (1992).

Kashima, N., et al. "Unique Structure of Murine Interleukin–2 as Deduced from Cloned cDNAs." *Nature (Lond.)* 313:402–404 (1985).

Weinberg, A., et al. "Recombinant Interleukin–2 as an Adjuvant for Vaccine–Induced Protection. Immunization of Guinea Pigs with Herpes Simplex Virus Subunit Vaccines." *J. Immunol.* 140:294–299 (1988).

Nunberg, J. H., et al. "Interleukin–2 Acts as an Adjuvant to Increase the Potency of Inactivated Rabies Virus Vaccine." *Proc. Natl. Acad. Sci. USA.* 86:4240–4243 (1989).

Takahashi, H., et al. "Induction of Broadly Cross–Reactive Cytotoxic T Cells Recognizing an HIV–1 Envelope Determinant." *Science (Wash DC)*. 255:333–336 (1992).

Flores–Villanueva, P. O., et al. "Recombinant IL–10 and IL–10/Fc Treatment Down–Regulate Egg Antigen–Specific Delayed Hypersensitivity Reactions and Egg Granuloma Formation in Schistosomiasis." *J. Immunol.* 156: 3315–3320 (1996).

Moreland, L. W., et al. "Treatment of Rheumatoid Arthritis with a Recombinant Human Tumor Necrosis Factor Receptor (p75)–Fc Fusion Protein." *N. Engl. J. Med.* 337: 141–147 (1997).

Zhao, Z., et al. "Controlled Delivery of Antigens & Adjuvants in Vaccine Development," *J. of Pharm. Sciences* 85(12):1261–1270 (1996).

Irvine, K. R., et al. "Cytokine Enhancement of DNA Immunization Leads to Effective Treatment of Established Pulmonary Melastases," *Journal of Immunology*, 238–245 (1996).

PROCESS FOR THE PRODUCTION OF BENZENE DERIVATIVES

BACKGROUND OF THE INVENTION

1. Field of the Invention

The present invention relates to a process for the production of benzene derivatives of chemical formula (I), which are useful as intermediates for agricultural chemicals, fine chemicals or pharmaceuticals such as anti-inflammatory analgesics.

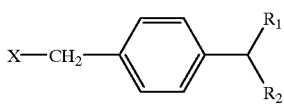

(I)

In chemical formula (I), X is a halogen, $R_1$ and $R_2$ are the same or different, $R_1$ is a hydrogen atom or lower alkyl radical of carbon number 1–6, $R_2$ is a hydrogen atom or $COOR_3$, and $R_3$ is a hydrogen atom or lower alkyl radical of carbon number 1–6.

2. Discussion of the Background

Benzene derivatives of the above chemical formula (I) are especially useful starting materials for the production of valuable 2-{4-(2-oxocyclopentylmethyl)phenyl} propionic acid, which is useful as an anti-inflammatory agent.

Several methods have been reported to produce benzene derivatives in aforesaid chemical formula (I).

According to Japan Public Patent No. 87-129250 and No. 87-155237, the reaction of 2-(para-methylphenyl)propionic acid and a halogenating agent under a radical generating agent has been disclosed.

In Japan Public Patent No. 81-13840, a method of producing 2-(4-halomethylphenyl) propionic acid by reaction of 2-phenylpropionic acid and methylal under a strong Lewis acid such as aluminum chloride ($AlCl_3$) and tin chloride ($SnCl_4$) has been disclosed.

In the aforesaid conventional methods, the purity of the final product is reduced due to the formation of by-products during the radical reaction. Consequently, a complicated refining process is required to improve the purity of the final product. In addition, in order to produce the starting material, 2-(para-methylphenyl)propionic acid, several reaction steps are required. Thus, the conventional processes are both complicated and expensive.

Therefore, it is desirable to provide a method of producing benzene derivatives of chemical formula (I) having improved purity from commercially available starting materials.

SUMMARY OF THE INVENTION

One object of the present invention is to provide a method for producing benzene derivatives of chemical formula (I) at low cost.

Another object of the present invention is to provide a method for producing benzene derivatives of chemical formula (I) having improved purity.

Another object of the present invention is to provide a method for producing benzene derivatives of chemical formula (I) having improved purity from commercially available starting materials.

Another object of the present invention is to provide a method for producing benzene derivatives of chemical formula (I) which are suitable as intermediates of agricultural chemical, fine chemical, or pharmaceuticals such as anti-inflammatory analgesics.

These and other objects have been achieved by the present invention which provides a method for the production of a benzene derivative represented by formula (I) by reacting a compound represented by formula (II) with a hydroformylating agent and a halogenating agent.

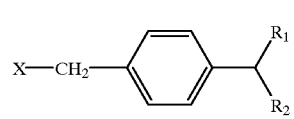

(I)

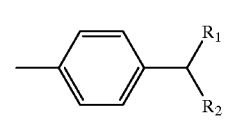

(II)

The first embodiment of the present invention relates to a process for producing a benzene derivative represented by formula (I), that includes:

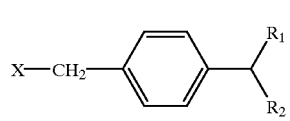

(I)

reacting a compound represented by formula (II) with a hydroformylating agent and a halogenating agent, wherein

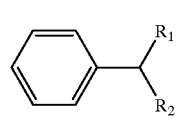

(II)

X is a halogen atom, $R_1$ and $R_2$ are the same or different, $R_1$ is a hydrogen atom or lower alkyl radical of carbon number 1–6, $R_2$ is a hydrogen atom or $COOR_3$ and $R_3$ is a hydrogen atom or lower alkyl radical of carbon number 1–6.

The second embodiment of the present invention relates to an improved process for producing 2-{4-(2-oxocyclopentylmethyl)phenyl} propionic acid by reacting a benzene derivative intermediate represented by formula (I),

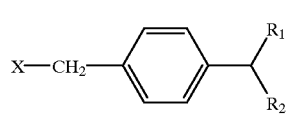

(I)

wherein the improvement includes:

producing the benzene derivative represented by formula (I) by a process that includes:

reacting a compound represented by formula (II) with a hydroformylating agent and a halogenating agent, wherein

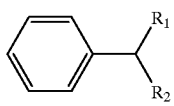

X is a halogen atom, $R_1$ and $R_2$ are the same or different, $R_1$ is a hydrogen atom or lower alkyl radical of carbon number 1–6, $R_2$ is a hydrogen atom or $COOR_3$ and $R_3$ is a hydrogen atom or lower alkyl radical of carbon number 1–6.

DESCRIPTION OF THE PREFERRED EMBODIMENTS

Various other objects, features and attendant advantages of the present invention will be more fully appreciated as the same becomes better understood from the following detailed description of the preferred embodiments, which are not intended to be limiting unless otherwise specified.

The preferred reaction sequence of the present invention is shown below. Reaction Formula 1:

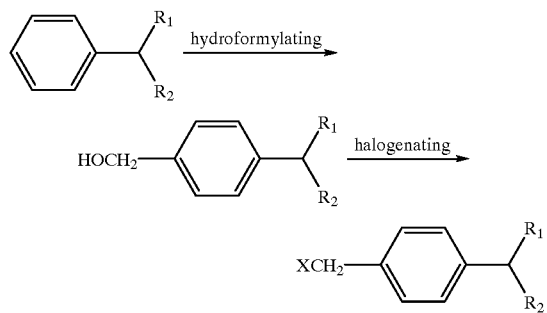

In chemical formulas (I) and (II), X is a halogen, $R_1$ and $R_2$ are the same or different, $R_1$ is a hydrogen atom or lower alkyl radical of carbon number 1–6, and $R_2$ is a hydrogen atom or $COOR_3$, and $R_3$ is a hydrogen atom or lower alkyl radical of carbon number 1–6.

The reaction conditions are not particularly limiting. Preferably, the above reaction is carried out for 2–30 hours at 40–140° C. More preferably, the reaction is carried out for 10–15 hours at 80–120° C.

Preferably, the reaction may be carried out in sequential steps or simultaneously. More preferably, the reaction is carried out simultaneously.

Preferred examples of hydroformylating agents are polymers capable of generating formaldehyde in a gaseous state or solution state, e.g., paraformaldehyde, formalin, trioxane (trimer of formaldehyde) or methylal (formaldehyde which is protected by methyl). The preferred quantity of hydroformylating agent to be added is 1–10 equivalents to 1 equivalent of the compound of chemical formula (II), the initiation substances. More preferably, the quantity of hydroformylating agent to be added is 2–4 equivalents to 1 equivalent of compound of chemical formula (II). In case the added quantity is less than 1 equivalent, the reaction does not proceed easily. If the added quantity is more than 10 equivalents, the economic effectiveness may be lowered.

Preferred examples of halogenating agents are hydrochloric acid, hydrobromic acid, hydroiodic acid, or metal halide in the presence of at least one of the aforementioned acids. In the halogenating agents, examples of metal halides are sodium chloride, sodium bromide, sodium iodide, potassium chloride, potassium bromide, potassium iodide, lithium chloride, or lithium bromide. The preferred quantity of halogenating agent to be added is 1.2–20 equivalents to 1 equivalent of compound of chemical formula (II). More preferably, the quantity of halogenating agent to be added is 5–10 equivalents. In case the added quantity is less than 1.2 equivalent, the reaction does not proceed easily. If the added quantity is over than 20 equivalents, the economic effectiveness may be lowered.

The reaction can also be performed in the presence of phase-transfer catalysts or in the absence of phase-transfer catalysts. Preferred examples of phase transfer catalysts are tetraalkylammonium halides, such as tetramethylammonium bromide, tetramethylammonium chloride, methyl triethylammonium bromide, benzyl triethylammonium chloride, tetradecyl trimethylammonium bromide, hexadecyl trimethylammonium bromide, or phenyl trimethylammonium chloride. Preferably, approximately 2–20 mole % of phase-transfer catalysts, more preferably, 1–10% based on the quantity of starting materials are employed.

The reaction may be performed with or without a solvent system, which is preferably inert under the reaction conditions. The solvent systems may be an organic solvent, or mixtures of organic solvent and organic acid, or organic acid and water, or a mixture of one or more organic solvents, organic acid and water. Preferred examples of organic solvents are methylene, chloroform, carbon tetrachloride, 1,2-dichloroethane, acetonitrile, 4-dioxane, tetrahydrofuran, cyclohexane, N,N-dimethylformamide or N,N-dimethylacetamide. Preferred examples of organic acids are sulfuric acid, acetic acid, phosphoric acid, trifluoroacetic acid, formic acid, methansulfonic acid or trifluoromethansulfonic acid. The preferred quantity of solvent is 0–50 equivalents to 1 equivalent of compound of chemical formula (II).

Preferred examples of the compound of chemical formula (II) are benzene, toluene, phenylacetic acid, 2-phenylpropionic acid, 2-phenylpropionic acid methyl ester or 2-{(4-chloromethyl)phenyl}propionic acid.

By equivalents, it is meant to mean molar equivalents or weight equivalents, according to the usage generally known in the art.

Upon completion of the reaction, the resulting product may be crystallized by adding solvent, recrystallized from solvent or purified by using silica gel column chromatography method after it has been extracted and concentrated.

In chemical formulas (I) and (II), lower alkyl radical is preferably an alkyl radical having a linear or branched chain, e.g., methyl, ethyl, propyl, isopropyl, n-butyl, and isobutyl, and the halogen atom is preferably chlorine, bromine, fluorine and iodide.

Preferred examples of benzene derivatives of chemical formula (I) are 2-(4-chloromethylphenyl) propionic acid, 2-(4-chloromethylphenyl) propionic acid methyl ester, 2-(4-chloromethylphenyl) propionic ethyl ester, 2-(4-bromomethylphenyl) propionic acid, 2-(4-bromomethylphenyl) propionic methyl ester or, 2-(4-bromomethylphenyl) propionic ethyl ester.

The benzene derivatives of chemical formula (I) produced in the process of the present invention may be used as intermediates for medicines, agricultural chemicals, or fine chemical products.

The benzene derivative of chemical formula (I) and the compound of formula (II) are optical isomers when $R_1$ and $R_2$ are different from each other. All optical isomers and their mixtures are expressed in the singular structural formulas (I) and (II) for convenience sake. The starting compound may be optically pure or a mixture of isomers to give, respectively, optically pure product or a mixture of isomers in the product.

EXAMPLES

Having generally described this invention, a further understanding can be obtained by reference to certain specific examples which are provided herein for purposes of illustration only and are not intended to be limiting unless otherwise specified.

Example 1

Benzene (16 g) was added to a mixture of acetic acid(25 ml) and hydrobromic acid (95 ml), followed by paraformaldehyde (12 g) and benzyltriethylammonium bromide (1.0 g). The mixture was then heated to 70° C. and stirred well at the same temperature for 24 hours. After cooling to room temperature, the mixture was extracted with dichloromethane and then concentrated to give oil residue. The oil residue was distilled under vacuum to give the target product, bromomethylbenzene (29 g). Result of measurement by NMR(CDCl$_3$, ppm) was 4.5(2H, s), 7.3(5H, m).

Example 2

Toluene (18 g) was added to a mixture of acetic acid (25 ml) and hydrobromic acid (95 ml), followed by trioxane (6.6 g) and benzyltriethylammonium bromide (2.0 g). The mixture was then heated to 70° C. and stirred well at the same temperature for 20 hours. After cooling to room temperature, the mixture was extracted with dichloromethane and then concentrated to give oil residue. The oil residue was distilled under vacuum to give the target product, 4-bromomethyltoluene (30.0 g). Result of measurement by NMR(CDCl$_3$, ppm) was 2.4(3H, s), 4.5(2H, s), 7.3(4H, dd).

Example 3

Phenylacetic acid (27 g) was added to a mixture of acetic acid (25 ml) and hydrochloric acid (95 ml), followed by paraformaldehyde (12 g) and hexadecyltrimethylammonium bromide (3.0 g). The mixture was then heated to 70° C. and stirred well at the same temperature for 26 hours.

After cooling to room temperature, the mixture was extracted with dichloromethane and then concentrated to give oil residue. The oil residue was distilled under vacuum to give the target product, 4-(chloromethyl) phenylacetic methylester (12.0 g). Result of measurement by NMR (CDCl$_3$, ppm) was 3.5(2H, s), 3.6(3H, s) 4.5(2H, s), 7.3(4H, dd).

Example 4

2-phenylpropionic acid (7.5) was added to a mixture of formic acid (7 ml) and hydrochloric acid (20 ml), followed by trioxane (4.5 g) and benzyltriethylammonium bromide (0.5 g). The mixture was then heated to 120° C. and stirred well at the same temperature for 30 hours. After cooling to room temperature, the mixture was extracted with ethylacetic acid and then concentrated to give oil residue. The oil residue was distilled and refined under vacuum to give the target product, 2-{(4-chloromethyl)phenyl} propionic acid (2.3 g). Result of measurement by NMR(CDCl$_3$, ppm) was 1.5(3H, d), 3.7(1H, q), 4.5(2H, s), 7.3(4H, dd).

Example 5

Pour 12.0 g 2-{(4-chloromethyl)phenyl}propionic acid and 15.0 g sodium iodide into 130 ml of methylethyl ketone, then be refluxed for 10 hours. Eliminate solvent under vacuum, and extract with ether. After washing the ether layer with sodium thiosulfate solution and water, 13.4 g of 2-{(4-iodomethyl)phenyl} propionic acid was obtained by evaporation and concentration. Result of measurement by NMR(CDCl$_3$, ppm) was 1.5(31H, d), 3.7(1H, q), 4.5(2H, s), 7.3(4H, dd).

Example 6

2-phenylpropionic acid (8.2 g) was added to a mixture of acetic acid (7 ml) and hydrobromic acid (40 ml), followed by trioxane (4.5 g) and hexadecyltrimethylammonium bromide (0.5 g). The mixture was then heated to 120° C. and stirred well at the same temperature for 19 hours. After cooling to room temperature, the mixture was extracted with ethylacetic acid and then concentrated to give oil residue. The oil residue was distilled and refined under vacuum to give the target product, 2-{(4-bromomethyl) phenyl} propionic acid (1.5 g). The result of measurement by NMR (CDCl$_3$, ppm) was 1.5(3H, d), 3.7(1H, q), 4.5(2H, s), 7.3(4H, dd).

Example 7

Pour 162 g of hydrochloric acid, 75 g of potassium chloride, 3 g of tetramethyl ammonium chloride, 18 g of paraformaldehyde orderly into 2-phenylpropionic acid, then reacted for 12 hours at 100° C. And after that cooled down at normal temperature. Add 200 g of purified water and ethyl acetate to reaction solution respectively, concentrated after the extraction of organic layer. After crystallization by adding 250 g of hexane, filtered the generated crystal, and drying, 33.3 g of 2-{(4-chloromethyl)phenyl}propionic acid was obtained.

The yield ratio on this experiment was 84%, and purity ratio measured by HPLC was 98.0%. Result of measurement by NMR(CDCl$_3$, ppm) was 1.5(3H, d). 3.7(1H, q), 4.7(2H, s), 7.3(4H, dd).

Example 8

Pour 162 g of hydrochloric acid, 75 g of potassium chloride, 3 g of tetramethyl ammonium chloride, 18 g of paraformaldehyde orderly into methyl 2-phenylpropionate, then reacted for 12 hours at 80° C. And after that cooled down at normal temperature. Add 200 g of purified water and ethyl acetate to reaction solution respectively. Concentrate after the extraction of the organic layer. 29.5 g of methyl{(4-chloromethyl)phenyl}propionate was obtained by distilling the reaction solution.

The yield ratio on this experiment was 74.3%, and purity ratio measured by HPLC was 98.5%. Result of measurement by NMR(CDCl$_3$, ppm) was 1.5(3H, d), 3.65(3H, s), 3.7(1H, q), 4.7(2H, s), 7.3(4H, dd).

Obviously, numerous modifications and variations of the present invention are possible in light of the above teachings. It is therefore to be understood that this invention may be practiced otherwise than as specifically described herein.

This application is based on Korean Patent Application No. 31040/97 filed Jul. 4, 1997, the entire contents of which are hereby incorporated by reference.

What is claimed is:

1. A process for producing a benzene derivative represented by formula (I), comprising:

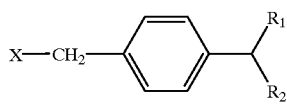

(I)

reacting a compound represented by formula (II) with a hydroformylating agent and a halogenating agent in the presence of at least one phase transfer catalyst, wherein

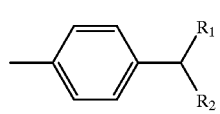

(II)

X is a halogen atom, $R_1$ and $R_2$ are the same or different, $R_1$ is a hydrogen atom or lower alkyl radical of carbon number 1–6, $R_2$ is a hydrogen atom or $COOR_3$ and $R_3$ is a hydrogen atom or lower alkyl radical of carbon number 1–6.

2. The process according to claim 1, wherein the hydroformylating agent is selected from the group consisting of paraformaldehyde, formalin, trioxane and methylal, and a mixture thereof.

3. The process according to claim 1, wherein the halogenating agent is selected from the group consisting of hydrochloric acid, hydrobromic acid, hydroiodic acid, and metal halides, and mixtures thereof.

4. The process according to claim 1, wherein the phase transfer catalyst is a tetraalkylammonium halide.

5. The process according to claim 1, wherein 1.0–10.0 equivalents of the hydroformylating agent are added to 1 equivalent of the compound represented by formula (II).

6. The process according to claim 1, wherein 1.2–20 equivalents of the halogenating agent are added to 1 equivalent of the compound represented by formula (II).

7. The process according to claim 1, wherein the reaction is carried out at a temperature of 40–140° C.

8. The process according to claim 1, wherein the reaction is carried out at a reaction time of 2–30 hours.

9. The process according to claim 1, wherein the benzene derivative represented by formula (I) is selected from the group consisting of 2-(4-chloromethylphenyl) propionic acid, 2-(4-chloromethylphenyl) propionic acid methyl ester, 2-(4-chloromethylphenyl) propionic ethyl ester, 2-(4-bromomethylphenyl) propionic acid, 2-(4-bromomethylphenyl) propionic methyl ester, and 2-(4-bromomethylphenyl) propionic ethyl ester.

10. The process according to claim 1, further comprising extracting the benzene derivative represented by formula (I).

11. The process according to claim 1, further comprising distilling the benzene derivative represented by formula (I).

12. In a process for producing 2-{4-(2-oxocyclopentylmethyl)phenyl}propionic acid by a reaction of a benzene derivative intermediate of the formula (I),

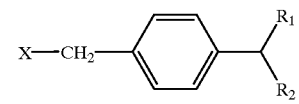

(I)

the improvement comprises:

producing said benzene derivative by a process, comprising:
reacting a compound represented by formula (II) with a hydroformylating agent and a halogenating agent in the presence of at least one phase transfer catalyst, wherein

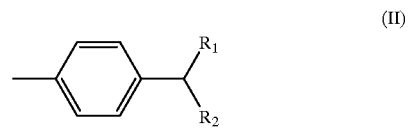

(II)

X is a halogen atom, $R_1$ and $R_2$ are the same or different, $R_1$ is a hydrogen atom or lower alkyl radical of carbon number 1–6, $R_2$ is a hydrogen atom or $COOR_3$ and $R_3$ is a hydrogen atom or lower alkyl radical or carbon number 1–6.

13. The process according to claim 12, wherein the hydroformylating agent is selected from the group consisting of paraformaldehyde, formalin, trioxane and methyl, and a mixture thereof.

14. The process according to claim 12, wherein the halogenating agent is selected from the group consisting of hydrochloric acid, hydrobromic acid, hydroiodic acid, and metal halides, and mixtures thereof.

15. The process according to claim 12, wherein the benzene derivative represented by formula (I) is selected from the group consisting of 2-(4-chloromethylphenyl) propionic acid, 2-(4-chloromethylphenyl) propionic acid methyl ester, 2-(4-chloromethylphenyl) propionic ethyl ester, 2-(4-bromomethylphenyl) propionic acid, 2-(4-bromomethylphenyl) propionic methyl ester, and 2-(4-bromomethylphenyl) propionic ethyl ester.

16. The process according to claim 12, further comprising extracting the benzene derivative represented by formula (I).

17. The process according to claim 12, further comprising distilling the benzene derivative represented by formula (I).

18. A process according to claim 1 wherein the compound of formula II is selected from the group consisting of benzene, toluene, phenylacetic acid, 2-phenylpropionic acid, 2-phenylpropionic acid methyl ester and 2-phenylpropionic acid ethyl ester.

19. A process according to claim 1 which is conducted in the absence of a Lewis acid catalyst.

* * * * *